US00PP33946P2

(12) United States Plant Patent
Beekenkamp

(10) Patent No.: US PP33,946 P2
(45) Date of Patent: Feb. 8, 2022

(54) ***DAHLIA* PLANT NAMED 'BKDAGPR'**

(50) Latin Name: *Dahlia hybrida*
Varietal Denomination: BKDAGPR

(71) Applicant: BEEKENKAMP PLANTS B.V., Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 17/346,278

(22) Filed: Jun. 13, 2021

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
CPC ... A01H 5/02; A01H 5/00; A01H 6/14; A01H 6/144
See application file for complete search history.

*Primary Examiner* — June Hwu
(74) *Attorney, Agent, or Firm* — C. Anne Whealy

(57) ABSTRACT

A new and distinct cultivar of *Dahlia* plant named 'BKDAGPR', characterized by its upright to somewhat outwardly spreading and sturdy plant habit; vigorous growth habit; freely branching habit; dense and bushy growth habit; dark green-colored leaves; freely flowering habit; and large semi-double type inflorescences with reddish purple-colored ray florets.

2 Drawing Sheets

Figure 1:
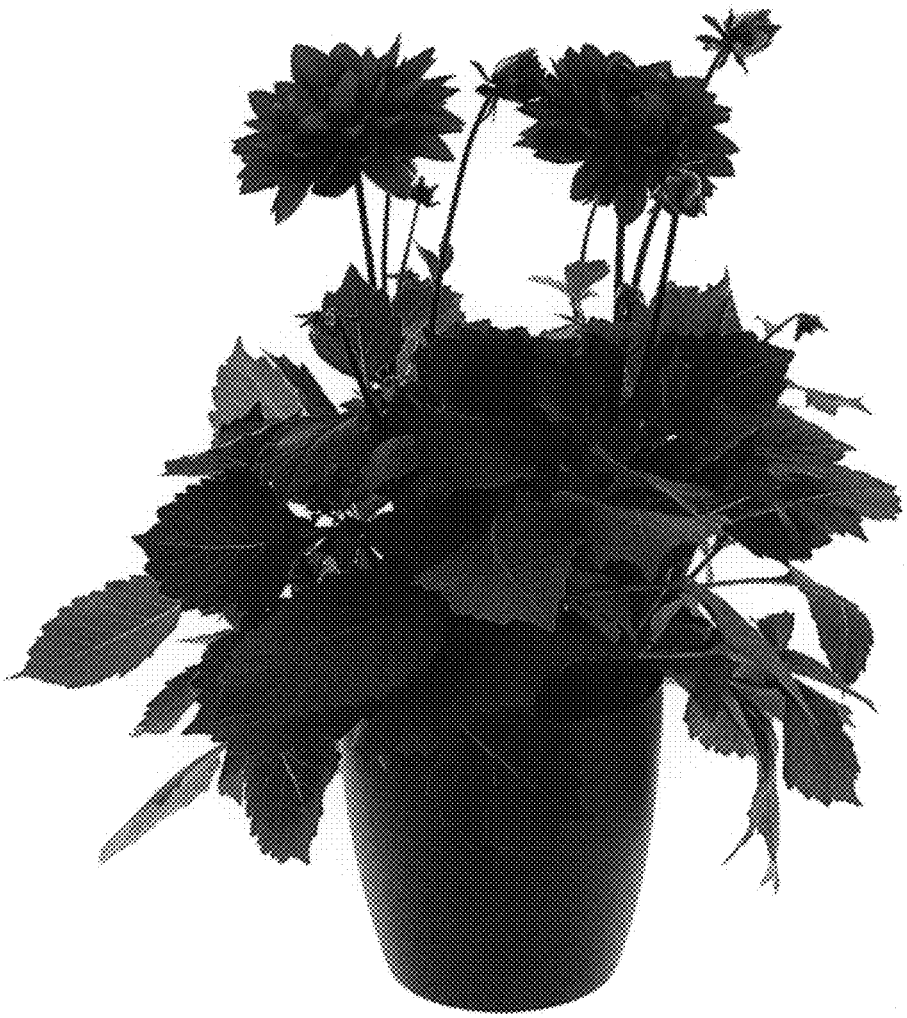

Botanical designation: *Dahlia hybrida.*
Cultivar denomination: 'BKDAGPR'.

STATEMENT REGARDING PRIOR DISCLOSURES BY INVENTOR/APPLICANT and ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Dahlia* plant, botanically known as *Dahlia hybrida* and hereinafter referred to by the name 'BKDAGPR'.

The new *Dahlia* plant is a product of a planned breeding program conducted by the Inventor in Maasdijk, The Netherlands. The objective of the breeding program is to create new freely branching container *Dahlia* plants with large inflorescences and attractive ray floret coloration.

The new *Dahlia* plant originated from an open-pollination in September, 2014 in Maasdijk, The Netherlands *Dahlia* sp. 'Datretten', disclosed in U.S. Plant Pat. No. 18,971, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled greenhouse environment in Maasdijk, The Netherlands in September, 2015.

Asexual reproduction of the new *Dahlia* plant by terminal cuttings in a controlled greenhouse environment in Maasdijk, The Netherlands since March, 2016 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAGPR'. These characteristics in combination distinguish 'BKDAGPR' as a new and distinct *Dahlia* plant:

1. Upright to somewhat outwardly spreading and sturdy plant habit.
2. Vigorous growth habit.
3. Freely branching habit; dense and bushy growth habit.
4. Dark green-colored leaves.
5. Freely flowering habit.
6. Large semi-double type inflorescences with reddish purple- colored ray florets.

Plants of the new *Dahlia* differ primarily from plants of the female parent, 'Datretten', in inflorescence type as plants of the new *Dahlia* have semi-double type inflorescences whereas plants of 'Datretten' have decorative type inflorescences. In addition, ray florets of plants of the new *Dahlia* are reddish purple in color whereas ray florets of plants of 'Datretten' are red and white in color.

Plants of the new *Dahlia* can be compared to plants of *Dahlia hybrida* 'BKDAPR', disclosed in U.S. Plant Pat. No. 23,278. In side-by-side comparisons, plants of the new *Dahlia* differ from plants of 'BKDAPR' in the following characteristics:

1. Plants of the new *Dahlia* are more open and not as sturdy as plants of 'BKDAPR'.
2. Ray florets of plants of the new *Dahlia* are reddish purple in color whereas ray florets of plants of 'BKDAPR' are dark red purple in color.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet (FIG. 1) is a side perspective view of a typical flowering plant of 'BKDAGPR' grown in a container.

Figure 2:
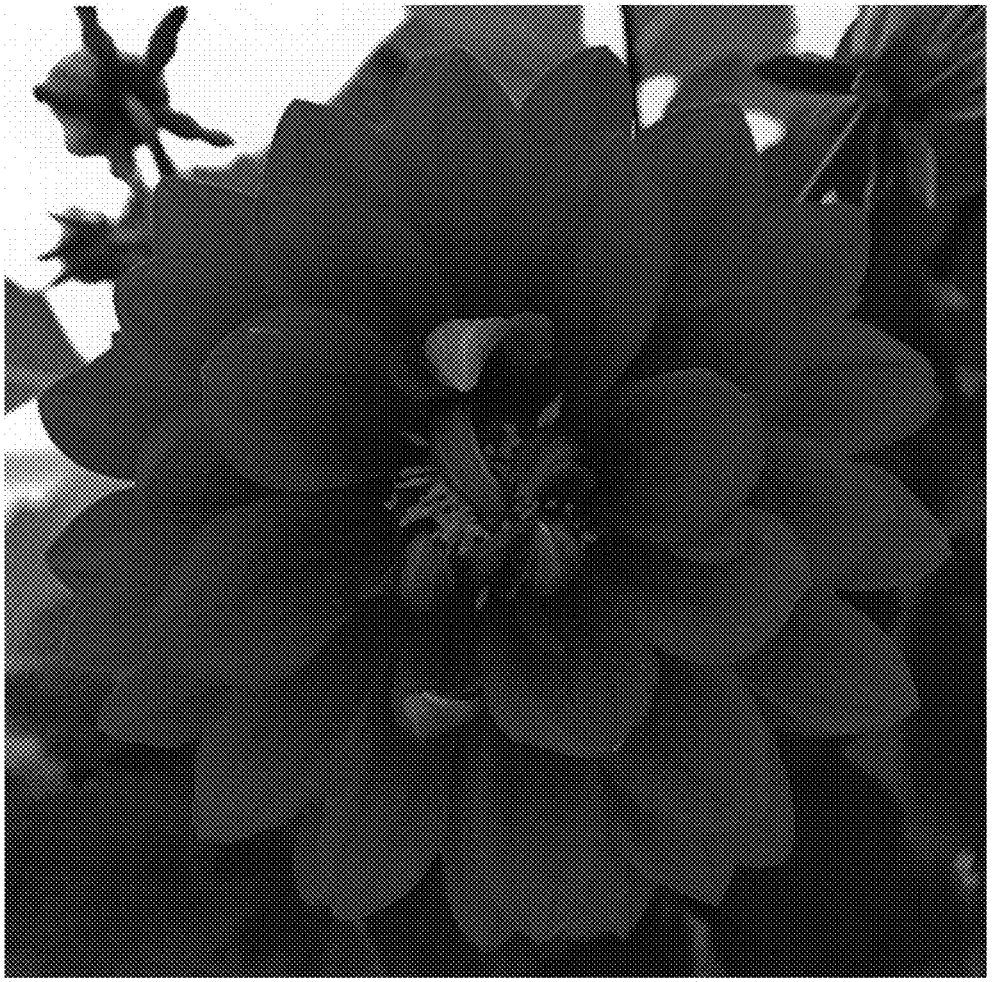

The photograph on the second sheet (FIG. 2) is a close-up view of a typical inflorescence of 'BKDAGPR'.

DETAILED BOTANICAL DESCRIPTION

The aforementioned photographs and the following observations and measurements describe plants grown during the winter and spring in 15-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were eight weeks from planting rooted cuttings when the photographs and description were taken. In the following description, color references are made to The Royal Horticultural Society Colour Chart, 2015 Edition, except where general terms of ordinary dictionary significance are used.

Botanical classification: *Dahlia hybrida* 'BKDAGPR'.

Parentage:

*Female, or seed, parent.*—*Dahlia* sp. 'Datretten', disclosed in U.S. Plant Pat. No. 18,971.

*Male, or pollen, parent.*—Unknown selection of *Dahlia hybrida*, not patented.

Propagation:

*Type.*—By terminal cuttings.

*Time to initiate roots, summer.*—About 16 days at temperatures ranging from 18° C. to 21° C.

*Time to initiate roots, winter.*—About 19 days at temperatures about 19° C. to 21° C.

*Time to produce a rooted young plant, summer.*—About 21 days at temperatures ranging from 18° C. to 21° C.

*Time to produce a rooted young plant, winter.*—About 23 days at temperatures ranging from 19° C. to 21° C.

*Root description.*—Medium in thickness, fibrous; typically white in color, actual color of the roots is dependent on substrate composition, water quality, fertilizers, substrate temperature and physiological age of roots; tuber development has not been observed on plants of the new *Dahlia*.

*Rooting habit.*—Moderately freely branching; medium density.

Plant description:

*Plant and growth habit.*—Upright to somewhat outwardly spreading plant habit; overall plant shape, roughly globular with inflorescences held above the foliar plane on strong peduncles; freely basal branching habit with about three primary branches each with about twelve secondary branches developing per plant; bushy and dense growth habit; pinching is not required but will improve branching habit; vigorous growth habit and moderate growth rate.

*Plant height, soil level to top of foliar plane.*—About 25.3 cm.

*Plant height, soil level to top of floral plane.*—About 39.9 cm.

*Plant diameter or spread.*—About 45.5 cm.

*Lateral branches.*—Length: About 13.2 cm. Diameter: About 7 mm. Internode length: About 5.4 cm. Aspect: Primary branches are about 30° from vertical; secondary branches are about 30° from primary branch axis. Strength: Moderately strong to strong. Texture and luster: Smooth, glabrous; glossy. Color, developing: Close to 144A. Color, developed: Close to 146A strongly tinged with a blend of N186C and 200B.

Leaf & leaflet description:

*Arrangement.*—Leaves opposite; simple and compound with typically three leaflets.

*Length, simple leaves.*—About 10.8 cm.

*Width, simple leaves.*—About 7.9 cm.

*Length, compound leaves.*—About 16.9 cm.

*Width, compound leaves.*—About 19.9 cm.

*Length, terminal leaflets.*—About 12.3 cm.

*Width, terminal leaflets.*—About 8.7 cm.

*Length, lateral leaflets.*—About 11.1 cm.

*Width, lateral leaflets.*—About 6.4 cm.

*Shape, simple leaves.*—Broadly ovate.

*Shape, compound leaves.*—Broadly ovate in outline.

*Shape, leaflets.*—Broadly ovate.

*Apex, simple leaves and leaflets.*—Broadly apiculate.

*Base, simple leaves and leaflets.*—Short to long attenuate.

*Margin, simple leaves and leaflets.*—Coarsely serrate to dentate.

*Venation pattern, simple leaves and leaflets.*—Pinnate.

*Texture and luster, upper surface, simple leaves and leaflets.*—Mostly smooth, glabrous with venation, moderately pubescent; not rugose; slightly glossy.

*Texture and luster, lower surface, simple leaves and leaflets.*—Sparsely pubescent; not rugose; matte.

*Color.*—Developing simple leaves and leaflets, upper surface: Close to a blend of 137A and 137B. Developing simple leaves and leaflets, lower surface: Close to a blend of 147B and 148B. Fully expanded simple leaves and leaflets, upper surface: Close to NN137A; venation, close to N144A. Fully expanded simple leaves and leaflets, lower surface: Close to 191A; venation, close to 146B.

*Petioles.*—Length, simple leaves: About 4.5 cm. Diameter, simple leaves: About 3 mm. Length, compound leaves: About 6.4 cm. Diameter, compound leaves: About 4 mm to 5 mm. Strength, simple and compound leaves: Moderately strong. Texture and luster, simple and compound leaves, upper and lower surfaces: Mostly smooth and glabrous; proximally, sparsely pubescent; glossy. Color, simple and compound leaves, upper surface: Close to 166A to a blend of N186C and 200A; towards the margins, close to 143B. Color, simple and compound leaves, lower surface: Close to 146B.

Inflorescence description:

*Appearance and arrangement*.—Large semi-double type inflorescences with ray and disc florets forming acropetally on a receptacle; inflorescences positioned above and beyond the foliar plane on strong peduncles; inflorescences face mostly upright to slightly outwardly; freely flowering habit with about 20 developing and fully developed inflorescences per plant at one time.

*Fragrance*.—None detected.

*Flowering response and flowering period*.—Early flowering habit, plants begin flowering about 62 days after planting; plants flower continuously during the autumn into the winter in The Netherlands.

*Post-production longevity*.—Inflorescences maintain good substance for about ten days on the plant; inflorescences persistent.

*Inflorescence buds*.—Height: About 1.4 cm. Diameter: About 3 cm. Shape: Flattened globular; involucral bracts slightly upright. Texture and luster: Smooth, glabrous; glossy. Color: Close to 144B; proximally, close to 144A slightly tinged with close to 173C to 173D; involucral bracts, close to 137B.

*Inflorescence size*.—Diameter: Large, about 12.1 cm. Depth (height): About 7 cm. Disc diameter: About 2.5 cm.

*Receptacles*.—Height: About 7 mm. Diameter: About 2 cm. Shape: Lunate. Color: Close to 144D.

*Ray florets*.—Quantity per inflorescence and arrangement: About 75 arranged in about five whorls. Length: About 4.6 cm. Width: About 1.9 cm. Shape: Obovate; moderately to strongly carinate and slight to moderately convex. Apex: Obtuse with a small abrupt acute tip, mucronate. Base: Cuneate. Margin: Entire. Aspect: Slightly upright to mostly horizontal. Texture and luster, upper surface: Smooth, glabrous; velvety; matte. Texture and luster, lower surface: Smooth, glabrous; slightly velvety; mostly matte with venation, slightly glossy. Color: When opening, upper surface: Close to a blend of N78A and N80A; towards the base, close to a blend of N78A and N79C. When opening, lower surface: Close to 77B; towards the margins, close to N80A. Fully opened, upper surface: Slightly darker and more intense than a blend of NN78A and N79C; towards the base, close to a blend of 71A and N79C; venation, similar to lamina color; with subsequent development, color becoming closer to N81A and towards the base, close to a blend of 60A and 187D. Fully opened, lower surface: Close to N78A; venation, close to N75D; with subsequent development, color becoming closer to 77B and towards the margins, close to N78A.

*Disc florets*.—Quantity per inflorescence and arrangement: About 60 massed at the center of the inflorescence in about five spiral whorls. Length: About 2.1 cm. Diameter: About 9 mm. Shape: Tubular, elongated; lower 93.5% fused and upper 6.5% free; apices, acute and reflexed. Texture and luster, inner and outer surfaces: Smooth, glabrous; glossy. Color, when opening, inner and outer surfaces: Apex: Close to 12A. Mid-section: Close to 12B. Base: Close to 155C. Color, fully opened, inner and outer surfaces: Apex: Close to 12A. Mid-section and base: Close to 155C.

*Phyllaries*.—Quantity per inflorescence and arrangement: About five to seven arranged in a single whorl. Length: About 2.1 cm. Width: About 7 mm. Shape: Oblanceolate; proximally, strongly carinate. Apex: Acute. Base: Cuneate. Margin: Entire. Texture and luster, upper and lower surfaces: Smooth, glabrous; glossy. Color, upper surface: Close to 143A. Color, lower surface: Close to 137B; venation, close to NN137A.

*Peduncles*.—Length, terminal peduncle: About 19.2 cm. Diameter, terminal peduncle: About 4 mm. Strength: Strong. Aspect: Mostly upright. Texture and luster: Smooth, glabrous; moderately glossy. Color: Close to 144A strongly tinged with close to a blend of N186C and 200B.

*Reproductive organs*.—Androecium, present on disc florets only: Quantity per floret: About five. Filament length: About 7 mm. Filament color: Close to 157D. Anther size: About 5 mm by 0.5 mm. Anther shape: Narrowly oblong. Anther color: Close to 15B. Pollen amount: Abundant. Pollen color: Close to N25C. Gynoecium, present on ray and disc florets: Quantity per floret: One. Pistil length: About 1.9 cm. Style length: About 1.5 cm. Style color: Close to 157D. Stigma diameter: About 9 mm. Stigma shape: Cleft. Stigma color: Close to 17A. Ovary color: Close to 145D. Seeds and fruits: To date, seed and fruit development have not been observed on plants of the new *Dahlia*.

Pathogen & pest resistance: To date, plants of the new *Dahlia* have not been observed to be resistant to pathogens and pests common to *Dahlia* plants.

Temperature tolerance: Plants of the new *Dahlia* have been observed to tolerate high temperatures of about 35° C. and to be suitable for USDA Hardiness Zones 9 to 11.

It is claimed:

1. A new and distinct *Dahlia* plant named 'BKDAGPR' as illustrated and described.

* * * * *